US005705396A

United States Patent [19]
Fickenscher et al.

[11] Patent Number: 5,705,396
[45] Date of Patent: Jan. 6, 1998

[54] ADDITIVE FOR DIAGNOSTIC TESTS FOR DETERMINATION OF THE COAGULABILITY OF BLOOD, METHOD OF REDUCING THE INFLUENCING OF DIAGNOSTIC TESTS BY HEPARIN AND THE USE OF METAL SALTS FOR THESE PURPOSES

[75] Inventors: Karl Fickenscher; Norbert Zander, both of Marburg, Germany

[73] Assignee: Behringwerke Diagnostics GmbH, Marburg, Germany

[21] Appl. No.: 516,198

[22] Filed: Aug. 17, 1995

[30] Foreign Application Priority Data

Aug. 20, 1994 [DE] Germany .................. 44 29 660.6

[51] Int. Cl.$^6$ .................................................. G01N 33/86
[52] U.S. Cl. ........................... 436/69; 436/18; 436/175; 435/13; 536/21
[58] Field of Search ..................... 436/8, 18, 69, 436/175; 422/73; 435/13; 536/21

[56] References Cited

U.S. PATENT DOCUMENTS

| | | | |
|---|---|---|---|
| 4,199,502 | 4/1980 | Babson et al. | 530/364 |
| 4,226,599 | 10/1980 | Butler et al. | 436/175 |
| 4,250,041 | 2/1981 | Babson et al. | 252/1 |
| 5,000,854 | 3/1991 | Yang | 210/638 |
| 5,039,529 | 8/1991 | Bergendal et al. | 536/21 X |
| 5,151,192 | 9/1992 | Matkovich et al. | 536/21 X |
| 5,286,388 | 2/1994 | Ingram | 436/178 X |
| 5,451,509 | 9/1995 | Speck | 435/13 |

FOREIGN PATENT DOCUMENTS

WO 88/09347 12/1988 WIPO.
WO 89/12692 12/1989 WIPO.

OTHER PUBLICATIONS

Gervin et al. *Clinical Research*, vol. 28(1), 1980, p. 90A.
Liu et al. *Thrombosis & Haemostasis*, vol. 66 (6), 1991, p. 742.
Liu et al. *Carbohydrate Research*, vol. 255, Mar. 4, 1994, pp. 183–191.
Stivala *Federation Proceedings*, vol. 36, No. 1, Jan. 1977, pp. 83–88.
Greenberg et al. *American Journal of Clinical Pathology*, vol. 86 (4), 1986, pp. 484–489.
Cumming et al., "In vitro neutralization of heparin in plasma prior to the activated partial thromboplastin time test: an assessment of four heparin antagonists and two anion exchange resins," Chemical Abstracts, vol. 104, No. 15 (Apr. 14, 1986), p. 340.
Kazama et al., "Modulation of protein C inhibitor activity by histidine–rich glycoprotein and platelet factor 4: role of zinc and calcium ions in the heparin–neutralizing ability of histidine–rich glycoprotein," Chemical Abstracts, vol. 116, No. 19 (May 11, 1992), p. 42.

Koide et al., "Effects of zinc and calcium ions on the neutralization by histidine–rich glycoprotein of the heparin–dependent activities of plasma proteinase inhibitors," Chemical Abstracts, vol. 115, No. 1 (Jul. 8, 1991), p. 5752.
Stivala et al., "Physicochemical studies of fractionated bovine heparin. IV. Copper(II) binding in relation to pH molecular weight and biological activity," Chemical Abstracts, vol. 67, No. 23 (Dec. 4, 1967), p. 115408.
Godal, H.C., "A Comparison Of Two Heparin–Neutralizing Agents: Protamine And Polybrene," Scandinav. J. Clin. & Lab. Investigation, vol. 12, pp. 446–457 (1960).
Grant et al., "$Zn^{2+}$ heparin interaction studied by potentiometric titration," Biochem J., vol. 287, pp. 849–853 (1992).
Grant et al., "Complexation of $Zn^{2+}$ ions by heparin," Biochemical Society Transactions, vol. 20, p. 363S (1992).
Jorpes et al., "Neutralisation Of Action Of Heparin By Protamine," The Lancet, vol. 2, pp. 975–976 (1939).
Lages et al., "Interaction of the Polyelectrolyte Heparin with Copper(II) and Calcium," Biopolymers, vol. 12, pp. 127–143 (1973).
Lindahl et al., "Glycosaminoglycans And Their Binding To Biological Macro–molecules," Ann. Rev. Biochem., vol. 47, pp. 385–417 (1978).
Mattai et al., "Quantitative similarity of zinc and calcium binding to heparin in excess salt solution," Biophysical Chemistry, vol. 31, pp. 295–299 (1988).
Parrish et al., "Selective binding of zinc ions to heparin rather than to other glycosaminoglycans," Biochem J., vol. 193, pp. 407–410 (1981).
Pedersen et al., "Inhibition of Recombinant Human Blood Coagulation Factor VIIa Amidolytic and Proteolytic Activity by Zinc Ions," Thrombosis and Haemostasis, vol. 65(5), pp. 528–534 (1991).
Speight et al., "Calcium Inhibits the Heparin–Catalyzed Antithrombin III/Thrombin Reaction by Decreasing the Apparent Binding Affinity of Heparin for Thrombin," Archives of Biochemistry and Biophysics, vol. 225, No. 2, pp. 958–963 (1983).
van den Besselaar et al., "Enzymatic elimination of heparin from plasma for activated partial thromboplastin time and prothrombin time testing," Blood Coagulation and Fibrinolysis, vol. 4, pp. 635–638 (1993).
Whitfield et al., "Heavy Metal Binding to Heparin Disaccharides. II. First Evidence for Zinc Chelation," Biopolymers, vol. 32, pp. 597–619 (1992).

*Primary Examiner*—Maureen M. Wallenhorst
*Attorney, Agent, or Firm*—Finnegan, Henderson, Farabow, Garrett & Dunner, L.L.P.

[57] ABSTRACT

The accuracy of a diagnostic test for determining the coagulability of blood is improved by reducing the interference by heparin. At least one metal salt, preferably a copper or zinc salt, is added to the diagnostic test to avoid or considerably reduce the undesirable influence of heparin on the test.

14 Claims, 3 Drawing Sheets

ADDITIVE FOR DIAGNOSTIC TESTS FOR DETERMINATION OF THE COAGULABILITY OF BLOOD, METHOD OF REDUCING THE INFLUENCING OF DIAGNOSTIC TESTS BY HEPARIN AND THE USE OF METAL SALTS FOR THESE PURPOSES

The present invention describes new possibilities, in particular additives for diagnostic tests and reagents, with which the influencing by heparin can be modified or suppressed. New methods and agents for modifying the sensitivity of diagnostic tests to heparin are described. In these, a metal salt which is capable of forming a complex with heparin and thereby reducing its activity is added either to one of the reagents or to the test batch itself. Influencing of the test by heparin can thus be either suppressed completely or adjusted to a desired level. Suitable metals are, for example, zinc or copper. In certain cases, a combination with heparin-neutralizing substances which are already known, such as polycations, may also lead to synergistic effects and therefore be advantageous.

BACKGROUND OF THE INVENTION

Heparins are polysulfated mucopolysaccharides having alternating hexosamine and hexuronic acid groups of different structure. They are isolated from the mucosa and lung of animals. The relative molecular masses vary between about 5,000 and 30,000, according to the source.

Heparin can bond to antithrombin III, thrombin and factor Xa and thereby greatly increase the rate of reaction between the protease and its inhibitor.

In blood plasma, heparin bonds to antithrombin III and thus turns this—slow-acting—"progressive inhibitor" into an "immediate inhibitor complex", which is active on blood coagulation.

In medicine, heparin is often employed as a therapeutic substance with which the coagulability of blood is reduced. The formation of thromboses and embolisms can thereby be prevented. The dosage must be monitored diagnostically in order, for example, to minimize the risk of hemorrhage. The tests most frequently employed for this purpose, such as thrombin time or activated partial thromboplastin time (aPTT), are as a rule too sensitive at somewhat higher dosages, so that the point in time of coagulation can no longer be determined.

The thrombin time is a control parameter in heparin treatment. The coagulation time of a citrate or oxalate plasma is measured after addition of a standardized amount of thrombin.

It is desirable to adjust the heparin sensitivity of these tests such that on the one hand they respond in the region of low heparin concentrations, but on the other hand still allow an evaluation in the region of higher heparin concentrations.

Other tests (for example the prothrombin time) show undesirable interferences with samples of patients under heparin treatment. In this case, complete elimination of the influence of heparin would be necessary. Measurement of the prothrombin time primarily serves to determine the activity of the vitamin K-dependent coagulation factors. If the heparin dosage is high, a prolonged coagulation time is found and reduced plasma contents of these coagulation factors are thus concluded. This can result in an unnecessary administration of preparations comprising these factors, so that the patients may be exposed to a treatment which is unnecessary and also carries a risk.

To exclude undesirable influences of heparin on diagnostic tests, heparin can be removed from the sample before carrying out the test.

It is known that samples can be freed from heparin by treatment with ion exchangers. In U.S. Pat. No. 5,000,854, Yang describes a process in which the heparin is removed from blood via protamine bonded to a carrier. U.S. Pat. No. 4,199,502 (Babson and Turner, 1980) describes a process in which a complex of protamine and serum albumin is added to the sample and the heparin containing precipitate formed after some time is then filtered off.

These processes are very time-consuming and adversely influence the samples in respect of their coagulation properties.

It is also possible to neutralize the heparin without removal from the sample. For this, polycations are added in a precisely metered amount to the sample. Complexes of the two oppositely charged macromolecules are then formed. By neutralization of its negative charges, heparin loses its efficacy. This was described for protamine as early as 1939 by Jorpes et al. (Lancet 2, 1939, 975–976). Other suitable substances were later described, thus, for example, polybrene (hexadimethrine bromide) by Godal (Scand.J.Clin. Lab. Invest. 12 (1960), 446–457).

The addition of polycations to the reagent or separate addition to the test batch would also be conceivable. These substances could be added to the plasma, a reagent or separately to the test batch. A disadvantage is, however, that because of their polycationic nature, they often react with constituents of the reagents and thus cause massive interference in the test. Thus, for example, they bond to phospholipid surfaces and neutralize the coagulation-promoting properties thereof. They usually therefore cannot be employed in test systems containing phospholipids, such as prothrombin time or aPTT. Their property of bonding heparin so firmly that its action is eliminated completely is also a disadvantage. It is therefore impossible to adjust a test system to a reduced heparin sensitivity for control and monitoring of a treatment.

Another possibility is that heparin may be broken down enzymatically by addition of the enzyme heparinase to the sample. Such a possibility is described in several instances in the literature, for example WO 89/12692. However, these processes are as a rule time-consuming, since the rate of cleavage of the enzyme is relatively low. Furthermore, an additional process step for breaking down the heparin is necessary. In this case also, it is not possible to adjust a test system to a reduced heparin sensitivity for control and monitoring of a treatment.

It has already been described that heparin forms bonds with various metal ions, for example Lages and Stivala, Biopolymers 12 (1973) 127–143. The complexes of heparin formed with calcium, copper and zinc have so far been characterized biophysically and biochemically above all in pure systems. The bonding can be used for purification of the heparin; thus, for example, an affinity chromatography step by utilization of the formation of a copper-heparin complex is described in WO 87/09547.

However, it has also already been described that heavy metals inhibit a number of enzymatic processes. Inhibition of factor VII activity by zinc has thus been investigated in detail (Pedersen et al., Thromb. Haemostasis 65(5); (1991); 528–534). It therefore does not seem appropriate to the expert to introduce such metal ions into diagnostic tests or reagents which are used for determination of blood coagulation, that is to say which are essentially also based on the function of enzymes.

The present invention was thus based on the technical problem of discovering a possibility of reducing or eliminating heparin sensitivity of coagulation tests which are known per se.

The solution to this technical problem is achieved by providing the embodiments characterized in the patent claims.

Surprisingly, however, it has been found in the context of the present invention that metal salts in a suitable concentration can nevertheless be employed to modify the heparin sensitivity of diagnostic reagents.

SUMMARY OF THE INVENTION

The present invention thus relates to additives for a test for determination of the coagulability of blood. Additives are understood as meaning those agents which can be added to a diagnostic test. They can be solvents or ready-made buffers which are either added to the test batch as an independent component or are already added to a reagent of the diagnostic test. The additives according to the invention comprise at least one metal salt, the metal ion of which can form a complex with heparin, whereby the interfering influence of heparin on the diagnostic test is prevented or at least considerably reduced.

BRIEF DESCRIPTION OF THE DRAWINGS

The figures show:

FIG. 1 shows the dependence of the prothrombin time on the heparin concentration for the three solvents of the prothrombin reagent.

The figure shows the thrombin times measured as a function of the heparin content of the sample and the zinc content of the buffer.

Figure 3:
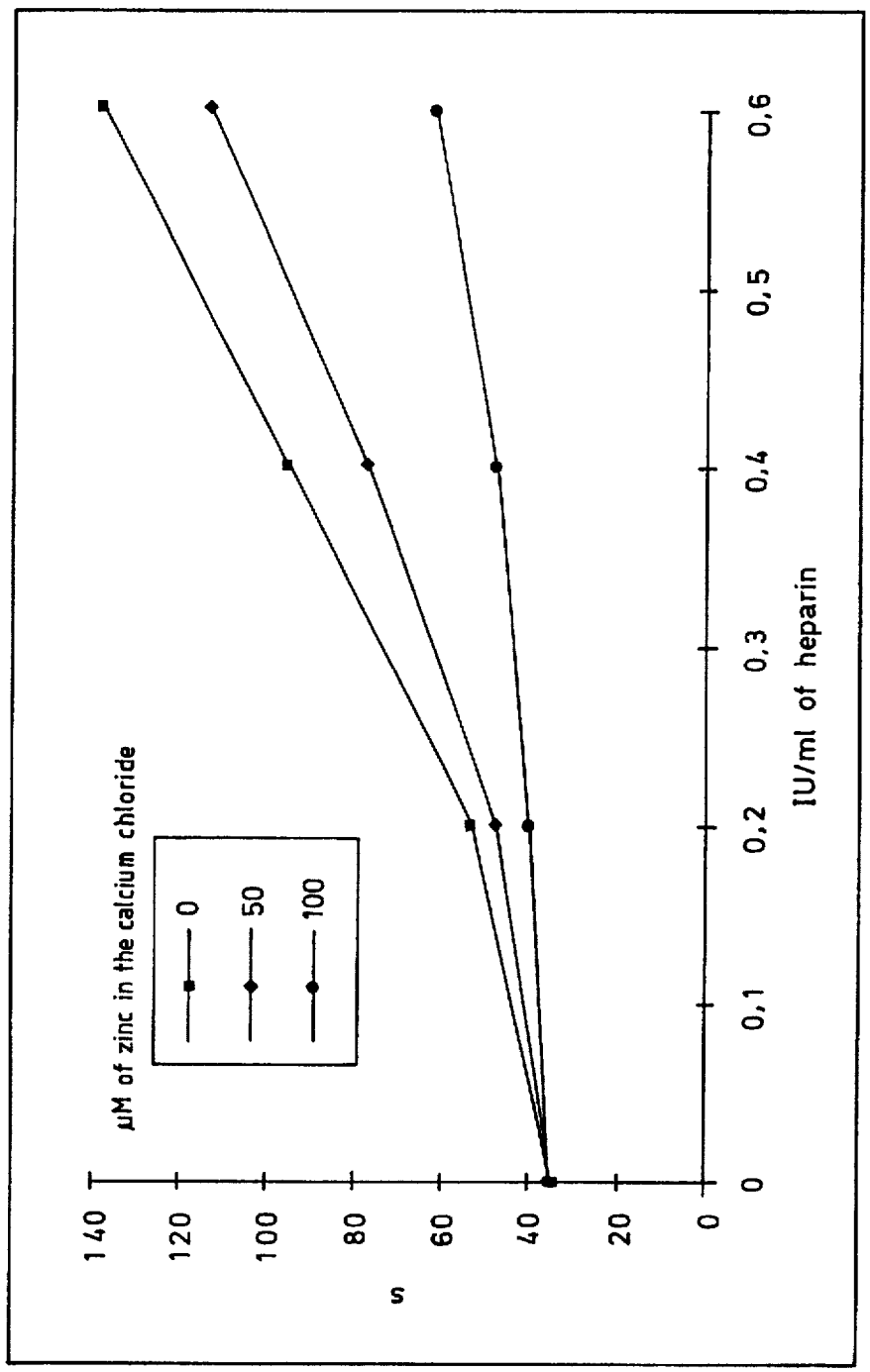

FIG. 3: Modification of the heparin sensitivity of the activated partial thromboplastin time by zinc Pathromtin was prepared as described in Example 3. A lyophilized human normal plasma pool was topped up with heparin (Liquemin, Roche) in concentrations of 0.1 IU/ml to 0.6 IU/ml.

FIG. 3 shows the aPTTs measured as a function of the heparin content of the sample and the zinc content of the starting reagent. Similar measurement values resulted for addition of zinc chloride to the activator reagent. The time measured is shown in second(s) in all three figures.

DETAILED DESCRIPTION OF THE INVENTION

The metals of the metal salt are preferably chosen from group 1 or group 2 of the Periodic Table of the Elements, the metals copper or zinc being particularly preferred.

The metal salts used according to the invention are employed in a concentration of greater than 0 up to 20 mM of metal salt. The Concentrations of the metal salts preferably vary in a range from 50 to 500 µM.

It has also been found that the surprising advantageous effect which can be achieved by the doctrine of the present invention can be further improved if, in addition to the metal salt, a polycation is added to the additive. A particularly preferred polycation here is Polybrene.

The present invention also relates to diagnostic reagents for determination of the thromboplastin time which comprise an additive according to the invention.

The invention also relates to those diagnostic reagents which comprise an additive according to the invention and are used for determination of the thrombin time or determination of the activated partial thromboplastin time.

In the context of the present invention, a method is also disclosed for reducing the influencing of a diagnostic test by heparin, in which an additive according to the invention is either incorporated into at least one reagent of the test batch or else added separately to the test batch.

The diagnostic tests are preferably processes for the determination of the coagulability of blood.

The present invention also relates to the use of an additive according to the invention for reducing the influencing of a diagnostic test for determination of the coagulability of blood by heparin.

The following examples serve to illustrate the invention. They demonstrate both the substantial elimination of the heparin effect on a test (Example 1) and synergistic effects with other heparin neutralizers which are already known (Example 1), as well as the possibility of adjusting the heparin sensitivity of a test system to a desired degree (Examples 2 and 3).

EXAMPLE 1

Heparin neutralization by addition of zinc chloride and/or Polybrene to a thromboplastin time reagent A normal plasma pool is topped up with heparin (Liquemin(R), Roche) in concentrations of 1 IU/ml to 4 IU/ml. A thromboplastin time reagent (Thromborel R, Behringwerke AG) is dissolved alternatively in:

a) water b) 100 µM zinc chloride c) 100 µM zinc chloride, 10 mg/l of Polybrene.

The thromboplastin time is determined in accordance with the manufacturer's instructions.

Figure 1:
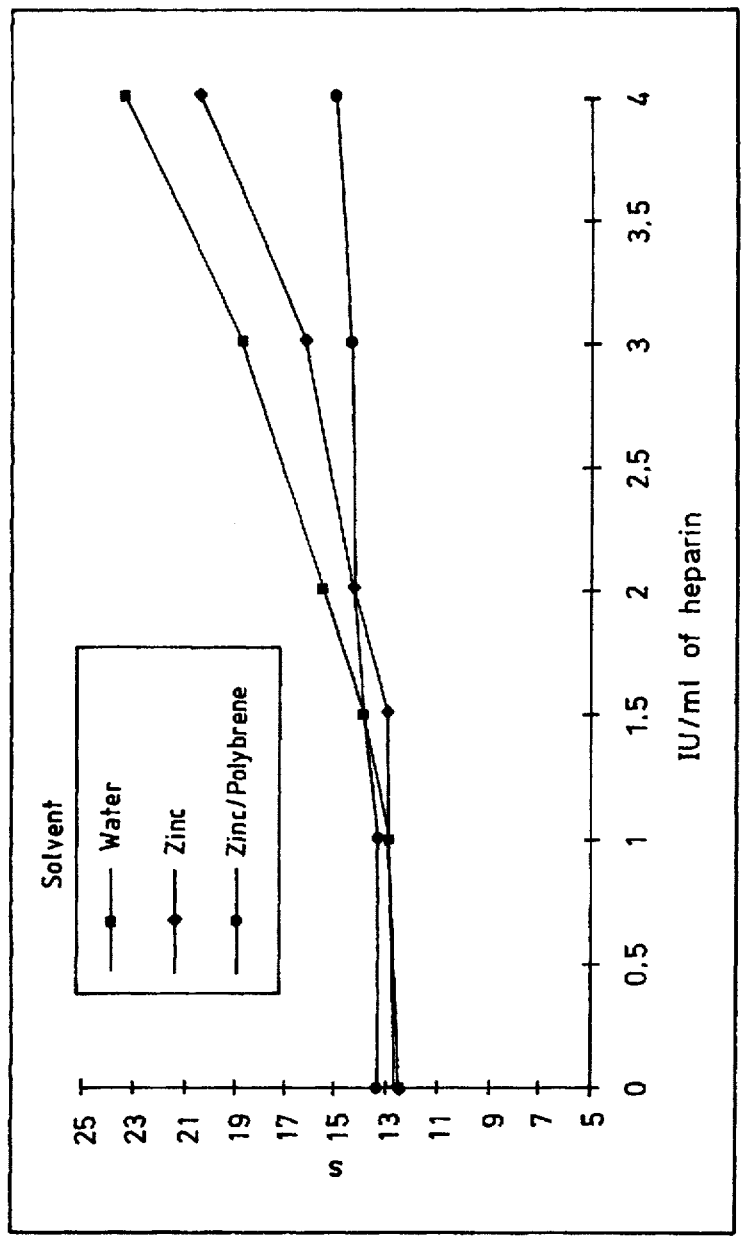
FIG. 1: Heparin neutralization by addition of zinc chloride and/or Polybrene to a thromboplastin time reagent Thromborel S was dissolved in various solvents as described in Example 1. A normal plasma pool was topped up with heparin (Liquemin(R), Roche) in concentrations of 1 IU/ml to 4 IU/ml.

FIG. 1 shows the dependence of the prothrombin time on the heparin concentration for the three solvents of the prothrombin time reagent. It can be clearly seen that when the additives b) and c) according to the invention are used, the interfering influence of heparin can be reduced significantly or excluded entirely.

EXAMPLE 2

Modification of the heparin sensitivity of a thrombin time reagent by zinc

A fresh plasma was topped up with heparin (Liquemin, Roche) in concentrations of 0.1 IU/ml to 0.6 IU/ml. A thrombin time reagent (Test-Thrombin-Reagenz, Behringwerke AG) was dissolved in a concentration of 3 IU/ml. The buffer intended for this reagent was topped up with zinc chloride in concentrations of 160 µM and 200 µM. The thrombin time determination was carried out as follows:

100 µl of sample

100 µl of buffer (where appropriate with zinc)

60 seconds incubation at 37° C.

100 μl of thrombin (3 IU/ml)

Measurement of the onset of coagulation.

Figure 2:
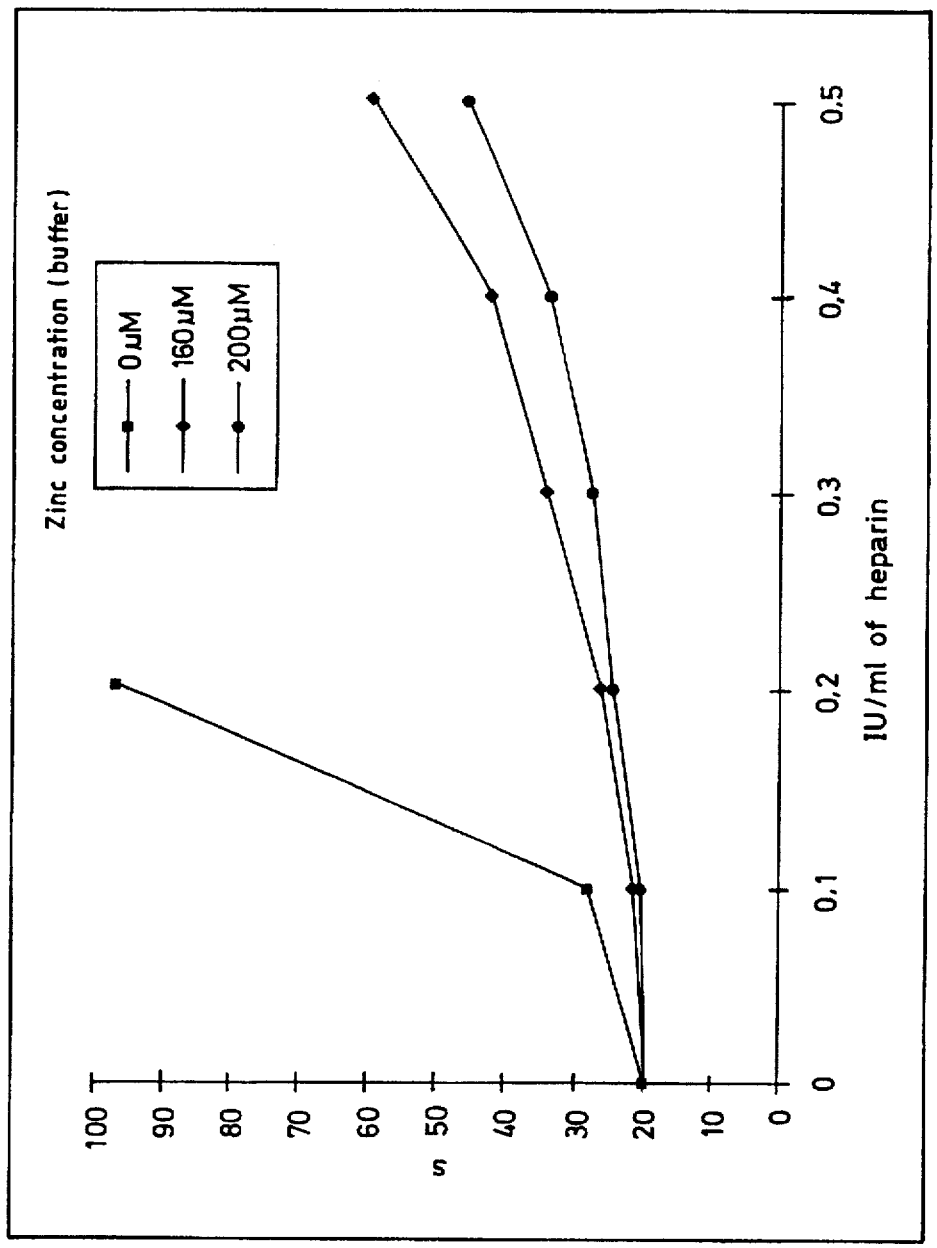
FIG. 2: Modification of the heparin sensitivity of a thrombin time reagent by zinc The Test-Thrombin reagent was dissolved as described in Example 2. Fresh plasma was topped up with heparin (Liquemin, Roche) in concentrations of 0.1 IU/ml to 0.6 IU/ml.

FIG. 2 shows the thrombin times measured as a function of the heparin content of the sample and the zinc content of the buffer. Specifically if the heparin concentration is relatively low, the interferences thereby caused can be excluded virtually completely.

EXAMPLE 3

Modification of the heparin sensitivity of the activated partial thromboplastin time by zinc A lyophilized human normal plasma pool was topped up with heparin (Liquemin, Roche) in concentrations of 0.1 IU/ml to 0.6 IU/ml. The aPTT was carried out with Pathromtin (Behringwerke AG) in accordance with the manufacturer's instructions. Zinc chloride was added either to the activator reagent or the starting reagent (calcium chloride) in concentrations of 50 μM and 100 μM.

FIG. 3 shows the aPTTs measured as a function of the heparin content of the sample and the zinc content of the starting reagent. Similar measurement values resulted for addition of the zinc chloride to the activator reagent.

We claim:

1. A method of reducing the interference by heparin with the accuracy of a diagnostic test for determining the coagulability of blood, which comprises introducing an additive into at least one reagent of said diagnostic test, wherein said additive comprises at least one metal salt of copper or zinc, a copper or zinc ion of which forms a bond with heparin.

2. A method of reducing the interference by heparin with the accuracy of a diagnostic test for determining the coagulability of blood, which comprises adding an additive to said diagnostic test, wherein said additive comprises at least one metal salt of copper or zinc, a copper or zinc ion of which forms a bond with heparin.

3. The method as claimed in claim 2, wherein said metal salt of copper or zinc is employed in a concentration of up to 20 mM.

4. The method as claimed in claim 3, wherein said metal salt of copper or zinc is employed in a concentration of between 50 and 500 μM.

5. The method as claimed in claim 4, wherein said metal salt of copper or zinc is zinc chloride and is employed in a concentration of 50 μM.

6. The method as claimed in claim 4, wherein said metal salt of copper or zinc is zinc chloride and is employed in a concentration of 100 μM.

7. The method as claimed in claim 4, wherein said metal salt of copper or zinc is zinc chloride and is employed in a concentration of 160 μM.

8. The method as claimed in claim 4, wherein said metal salt of copper or zinc is zinc chloride and is employed in a concentration of 200 μM.

9. The method as claimed in claim 4, wherein said additive further comprises at least one polycation.

10. The method as claimed in claim 9, whereto said polycation is Polybrene.

11. The method as claimed in claim 10, wherein said Polybrene is employed in a concentration of 10 mg/l, and said metal salt of copper or zinc is zinc chloride and is employed in a concentration of 100 μM.

12. The method as claimed in claim 2, wherein said diagnostic test determines thromboplastin time.

13. The method as claimed in claim 2, wherein said diagnostic test determines thrombin time.

14. The method as claimed in claim 2, wherein said diagnostic test determines activated partial thromboplastin time.

* * * * *

UNITED STATES PATENT AND TRADEMARK OFFICE
CERTIFICATE OF CORRECTION

PATENT NO. : 5,705,396
DATED : January 06, 1998
INVENTOR(S) : Karl FICKENSCHER et al.

It is certified that error appears in the above-indentified patent and that said Letters Patent is hereby corrected as shown below:

Claim 10, column 6, line 22, "whereto" should read --wherein--.

Signed and Sealed this

Ninth Day of June, 1998

Attest:

BRUCE LEHMAN

Attesting Officer

Commissioner of Patents and Trademarks